United States Patent
Lemberg (10) Patent No.: US 6,419,671 B1
(45) Date of Patent: Jul. 16, 2002

(54) OPTICAL FEEDBACK SYSTEM FOR VISION CORRECTION

(75) Inventor: Vladimir Lemberg, Redwood City, CA (US)

(73) Assignee: VISX, Incorporated, Santa Clara, CA (US)

( * ) Notice: Subject to any disclaimer, the term of this patent is extended or adjusted under 35 U.S.C. 154(b) by 0 days.

(21) Appl. No.: 09/470,907

(22) Filed: Dec. 23, 1999

(51) Int. Cl.[7] .............................................. A61B 18/18
(52) U.S. Cl. ................. 606/5; 606/6; 606/11; 606/4
(58) Field of Search .................. 606/4–6, 10–13, 606/17–18; 351/205, 206, 212

(56) References Cited

U.S. PATENT DOCUMENTS

| | | | |
|---|---|---|---|
| 4,579,430 A | * 4/1986 | Bille | 351/206 |
| 4,724,522 A | 2/1988 | Belgorod | |
| 4,941,093 A | * 7/1990 | Marshall et al. | 364/413.01 |
| 5,071,417 A | * 12/1991 | Sinofsky | 606/8 |
| 5,284,477 A | 2/1994 | Hanna et al. | |
| 5,325,133 A | * 6/1994 | Adachi | 351/209 |
| 5,423,801 A | * 6/1995 | Marshall et al. | 606/5 |
| 5,608,472 A | * 3/1997 | Szirth et al. | 351/206 |
| 5,624,436 A | 4/1997 | Nakamura et al. | |
| 5,653,706 A | * 8/1997 | Zavislan et al. | 606/9 |
| 5,720,894 A | * 2/1998 | Neev et al. | 216/65 |
| 5,777,719 A | * 7/1998 | Williams et al. | 351/212 |
| 5,787,890 A | 8/1998 | Reiter et al. | |
| 5,803,923 A | 9/1998 | Sinh-Derewa et al. | |
| 5,909,270 A | 6/1999 | Moser et al. | |
| 6,004,313 A | * 12/1999 | Shimmick et al. | 606/5 |
| 6,063,071 A | * 5/2000 | Nolan | 606/4 |

OTHER PUBLICATIONS

Product Brochure for IDL, The Interactive Data Language, Research Systems, Inc., 4990 Pearl East Circle, Boulder, CO, 80301, telephone: 303–786–9900, (1998) 3 pages total.
Kodak Megaplus Cameras, High Resolution CCD Digital Cameras, Eastman Kodak Company, Motion Analysis Systems Division, 11633 Sorrento Valley Road, San Diego, CA 92121, telephone: 800–462–4307, (1999) 2 pages total from http://www.kodak.com/cgi–bin/webCa . . . ustrial+Camera+Products+(MEGAPLUS).
The Photonics Dictionary™ (1997) 5 pages total.
Smith et al., The Eye and Visual Optical Instruments, Cambridge University Press, (1997) pp. 662–664, 666, 670, 690–693.
Stanley et al., Digital Signal Processing, Reston Publishing, Reston, VA, (1984) Chapter 4, pp. 120–124.

* cited by examiner

Primary Examiner—Roy D. Gibson
Assistant Examiner—Peter J Vrettakos
(74) Attorney, Agent, or Firm—Townsend and Townsend Crew LLP (57) ABSTRACT

The invention provides laser eye surgery devices, systems, and methods which measure the refractive error in the eye before, during, and/or after vision correction surgery. The invention allows adjustments during the vision correction operation, and allows qualitative and/or quantitative measurements of the progress of photorefractive treatments by projecting and imaging reference images though the cornea and other components of the ocular optical system. A slope of an image quality value such as an Optical Transfer Function may be monitored during the procedure to help determine when to terminate treatment.

25 Claims, 8 Drawing Sheets

OPTICAL FEEDBACK SYSTEM FOR VISION CORRECTION

BACKGROUND OF THE INVENTION

The present invention relates generally to vision correction systems. In one embodiment, the present invention relates to a simplified optical feedback system which can be integrated into existing laser eye surgery systems to provide feedback regarding the progress of the changes in refractive characteristics of the eye, optionally allowing real-time measurements of the rate of change in quality of the ocular optical system of the eye during vision correction surgery.

Known laser eye procedures generally employ an ultraviolet or infrared laser to remove a microscopic layer of stromal tissue from the cornea of the eye to alter the refractive characteristics of the eye. The laser removes a selected portion of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye.

Although known algorithms have generally been successful in calculating the pattern of laser energy to apply to correct standard vision errors, current vision correction systems would be further improved if they could monitor the changes actually taking place during a photorefractive procedure. Known ablation algorithms often assume a uniform ablation rate, so that each pulse of laser energy is expected to remove a uniform depth of corneal tissue. Although this is often a valid approximation, ablation depths may vary significantly with changes in environmental conditions, such as at different humidities or the like. Ablation depths may also vary locally, such as with the phenomenon called "central islands," a slightly reduced central ablation depth sometimes experienced within a large area ablation. As a result of ablation depth inconsistencies, touch-up procedures are sometimes performed following laser surgery after the eye has healed in order to further reshape the cornea and provide the desired vision performance. Furthermore, as healing can take several months, these touch-up surgeries can create a substantial inconvenience for a patient. To avoid this delay, laser surgery systems would benefit greatly from having some type of concurrent feedback.

Treatment of still further refractive errors of the eye have also been proposed, including treatment of irregular corneas and the like. Hartmann-Shack wavefront sensor topography devices are now being developed to accurately measure the optical characteristics of the eye. Theoretically, custom ablation patterns derived from such measurement systems may allow correction of small irregular errors with sufficient accuracy to reliably provide visual acuities of better than 20/20. Unfortunately, the wavefront sensors proposed to date have been quite bulky, so that it may be difficult and/or impossible to incorporate these measurement devices into the existing laser surgery systems now in use. While it may be possible to include an alternative off-axis cornea measurement system in known treatment devices, the accuracy of such off-axis systems may not be as good as desired, particularly for treatment of minor irregular errors of the eye so as to maximize visual acuity. Hence, alternative techniques are needed to provide feedback on the actual progress of an ablation. Such feedback techniques might provide substantial benefits over conventional procedures, where a patient generally waits for the epithelium or flap covering the ablated stromal surface to heal before the eye is further evaluated and before "touch up" surgery can be performed to further reshape the cornea.

In light of the above, it would be desirable to provide improved ophthalmological systems, devices, and methods. It would be particularly desirable to provide enhanced techniques for verifying the success of a laser eye surgery procedure. It would further be desirable if these devices could be easily integrated into existing laser eye surgery systems, as well as in newly developed surgery systems. At least some of these objectives will be met by the system and method of the present invention described hereinafter and in the claims.

SUMMARY OF THE INVENTION

The present invention provides improved laser eye surgery devices, systems, and methods. More particularly, the present invention provides devices, systems and methods which can provide measurements of the refractive error in the eye before, during, and/or after vision correction surgery, often while the patient is positioned for laser treatment and aligned with the laser delivery system. The present invention allows adjustments to be made during the vision correction operation, without having to wait for post-surgery analysis regarding the success of the surgery. This is particularly useful when the patient's eye has unusual characteristics which may not have been accounted for and/or if there are unanticipated difficulties in the operation, such as an error in measuring the original patient prescription, human operator error, variations in humidity, or the like. By taking advantage of a relatively simple system for determining the optical properties of a patients eye, with many of the system components already being included on known laser treatment workstations, the present invention may be used to provide vision better than 20/20.

In a first aspect, the invention provides an eye treatment system for performing vision correction on an eye. The eye has retina and ocular optics including a cornea. The system comprises projection optics arranged to project a reference image through the ocular optics and onto the retina when the eye is positioned for treatment. Imaging optics are oriented to acquire an evaluation image from the retina through the ocular optics. The evaluation image is defined by the reference image as projected through the ocular optics and imaged through the ocular optics. An energy transmitting element is positioned relative to the imaging optics to transmit treatment energy toward the cornea for altering the ocular optics.

In many embodiments, at least a portion of the portion of the projection optics and/or the imaging optics will be coaxially aligned with the treatment energy. Typically, the energy transmitting element comprises a laser, with the energy comprising a corneal ablation laser beam directed along a beam path. Beam splitters can be provided to separate the beam path from an imaging path of the imaging optics, a projection path of the projection optics, and the like, with the projection and imaging paths each having at least a portion coaxially aligned with the beam path of the laser beam.

Advantageously, the imaging optics may comprise a microscope such as the microscopes often included in laser eye surgery systems to image the cornea for optically directing a resculpting procedure. Such corneal imaging microscopes may be modified to allow imaging of the evaluation image from the retina by including additional and/or selectable lenses along the imaging path, by providing sufficient travel of movement of the microscope body, or the like. Typically, an imaging beam splitter will separate a microscope optical path from the imaging path before the image reaches the eyepiece of the microscope.

In many embodiments, an image capture device such as a Charge Couple Device (CCD) will be optically coupled to the imaging system to generate signals in response to the analysis image. An image analyzer will often be coupled to the image capture device, with the image analyzer generally determining an imaging quality of the ocular optics. The image analyzer will often be coupled to the energy transmitting element to define a corneal treatment feedback path. In many embodiments, a reference object will define the reference image and the image analyzer will compare an image of the reference object to determine the imaging quality. The analyzer will often calculate the imaging quality using a modulation transfer function, the analyzer ideally calculating a rate of change of the imaging quality (such as a slope of the image quality relative to the treatment energy directed to the cornea), so that the system can terminate the treatment energy at or below a predetermined (often low) rate of change of the imaging quality.

In some embodiments, the projection optics will include at least one moveable element to adjust a focal distance between the eye treatment system and the projected reference. Optionally, the eye surgery system may include a patient target fixation system which makes use of at least a portion of the projection optics. The target system may be capable of directing a fixation target toward the eye for viewing by the eye so as to help the patient maintain axial alignment between the eye and the treatment energy. Optionally, the at least one moveable element may be adjusted during treatment of the eye while monitoring the analysis image so as to help determine the change in refractive properties actually effected by the treatments. In a simple embodiment, the system operator may vary the projection focal distance between treatments so as to estimate one or more optical characteristic (such as quality, power, or the like) and/or one or more rate of change of an optical characteristic effected by a partial treatment of the eye.

In another aspect, the invention provides a method for performing vision correction on an eye. The method comprises aligning the eye relative to a treatment axis of a treatment system. A refractive characteristic of the eye is changed by directing a laser beam along the treatment axis and onto a cornea of the eye. An image is projected onto a retina of the aligned cornea through an ocular optic system, the ocular optic system including the cornea. The projected image from the retina is imaged through the ocular optic system, and the laser beam is controlled at least in part in response to the imaging step.

Preferably, an optical imaging quality of the ocular optical system will be determined based on an analysis image defined by the imaging step. The imaging quality will often be determined by comparing the analysis image with a reference image, typically using an optical transfer function or the like. In the exemplary embodiment, a rate of change of the imaging quality will be determined, which can thereby indicate combined distortions associated with a first pass of the projected image through the ocular optical system and onto the retina, as well as a second pass of the image through the ocular optical system from the retina to the imaging system. The optical imaging quality and/or its rate of change may be calculated by a processor, or may simply be monitored by a system operator. Regardless, this can provide a feedback indication of the progress of the actual ablation procedure during laser eye surgery.

A further understanding of the nature and advantages of the invention will become apparent by reference to the remaining portions of the specification and drawings.

DESCRIPTION OF THE SPECIFIC EMBODIMENTS

The present invention provides systems and methods which can provide measurements of the refractive error in the eye before, during, or after vision correction surgery. The present invention is particularly useful for enhancing the accuracy and efficacy of laser eye surgical procedures such as photorefractive keratectomy (PRK), phototherapeutic keratectomy (PTK), laser in situ keratomileusis (LASIK), and the like. Preferably, the present invention can provide real time measurements of the improvement of the optical system in the eye and provide feedback to surgeons during the vision correction procedures. Hence, although the system is described in the context of a laser eye surgery system, it should be understood the system may be adapted for use in alternative eye treatment procedures systems such as radial keratotomy, corneal ring implants, and the like.

The system of the present invention can be easily adapted to existing laser systems, in part because the components of the system can operate through a beamsplitter directing energy from a laser beam delivery device to the eye. By providing feedback and graphical information on actual progress of improvements of the optical system in the eye, the system operator can continue the vision correction surgery until the eye is at or near its maximum level of imaging performance as indicated by the feedback device. The present invention also allows the surgeon to evaluate progress during the surgery, and typically does not require that the surgery be interrupted and/or alignment of the eye with the treatment system be altered to perform evaluations. Thus, the use of the present optical feedback system may facilitate resculpting of the cornea so that the eye exceeds the normal 20/20 threshold of desired vision.

Figure 1:
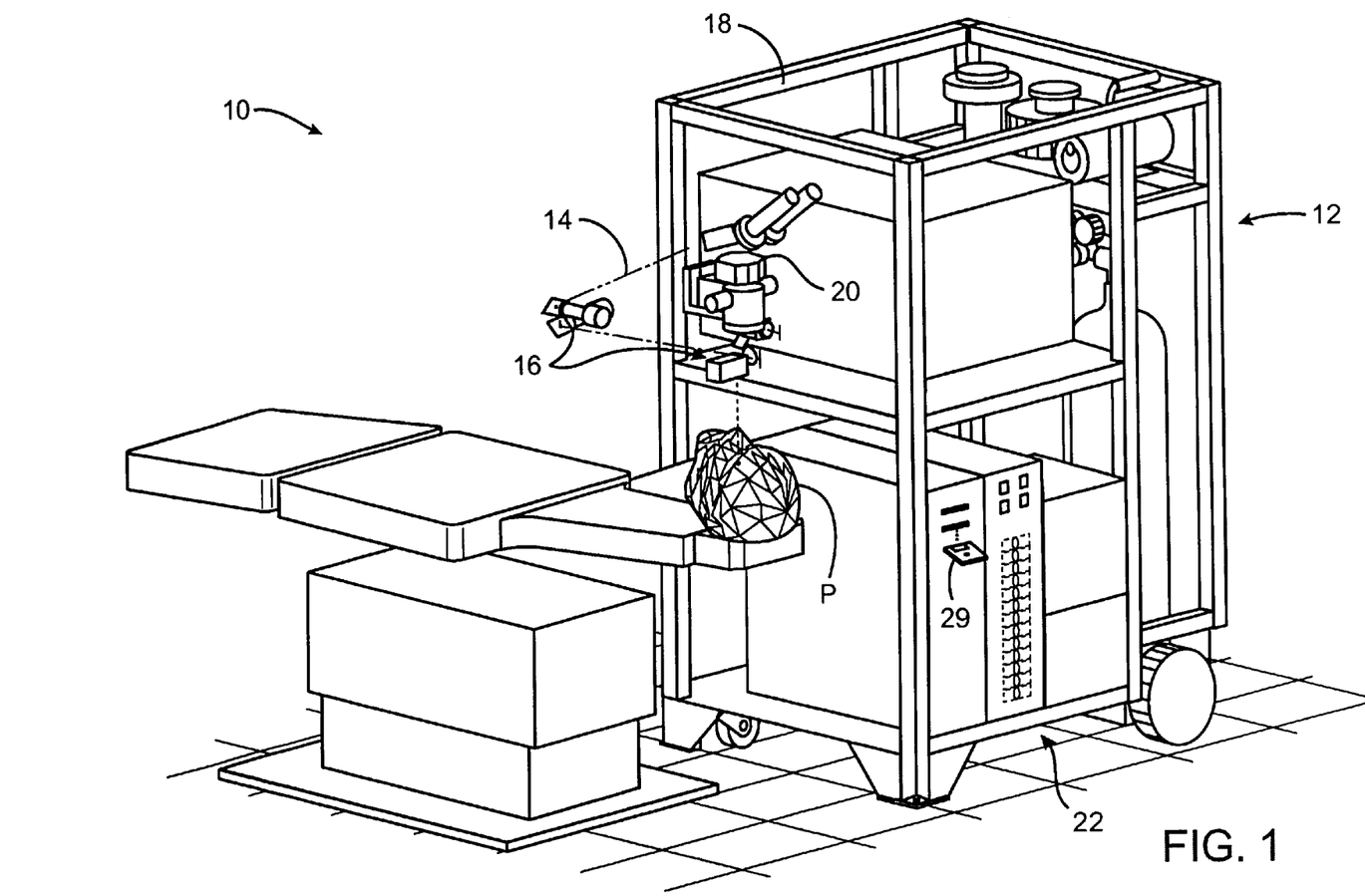
FIG. 1 is a perspective view of a laser eye surgery system according to the principles of the present invention.

Referring now to FIG. 1, a laser eye surgery system 10 of the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of eye E. Optionally, at least some of the optical components of microscope 20 may also be used to image a retina of the eye, as described in detail below.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye of patient P under the direction of a computer 22. Computer 22 will generally selectively adjust laser beam 14 to expose portions of the cornea to the pulses of laser energy so as to effect a predetermined resculpting of the cornea and alter the refractive characteristics of the eye. In many embodiments, both laser 14 and the laser delivery optical system 16 will be under computer control of processor 22 to effect the desired laser sculpting process, with the processor ideally altering the ablation procedure in response to inputs from the optical feedback system described hereinbelow. The feedback will preferably be input into processor 22 from an automated image analysis system, or may be manually input into the processor by a system operator using an input device in response to a visual inspection of analysis images provided by the optical feedback system. Processor 22 will often continue and/or terminate a resculpting treatment in response to the feedback, and may optionally also modify the planned resculpting based at least in part on the feedback Laser beam 14 may be adjusted to produce the desired resculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. Nos. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. Nos. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As mentioned above, laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, or the like, and the processor 22 will include the memory boards and other standard components of modem computer systems for storing and executing this code.

Figure 2:
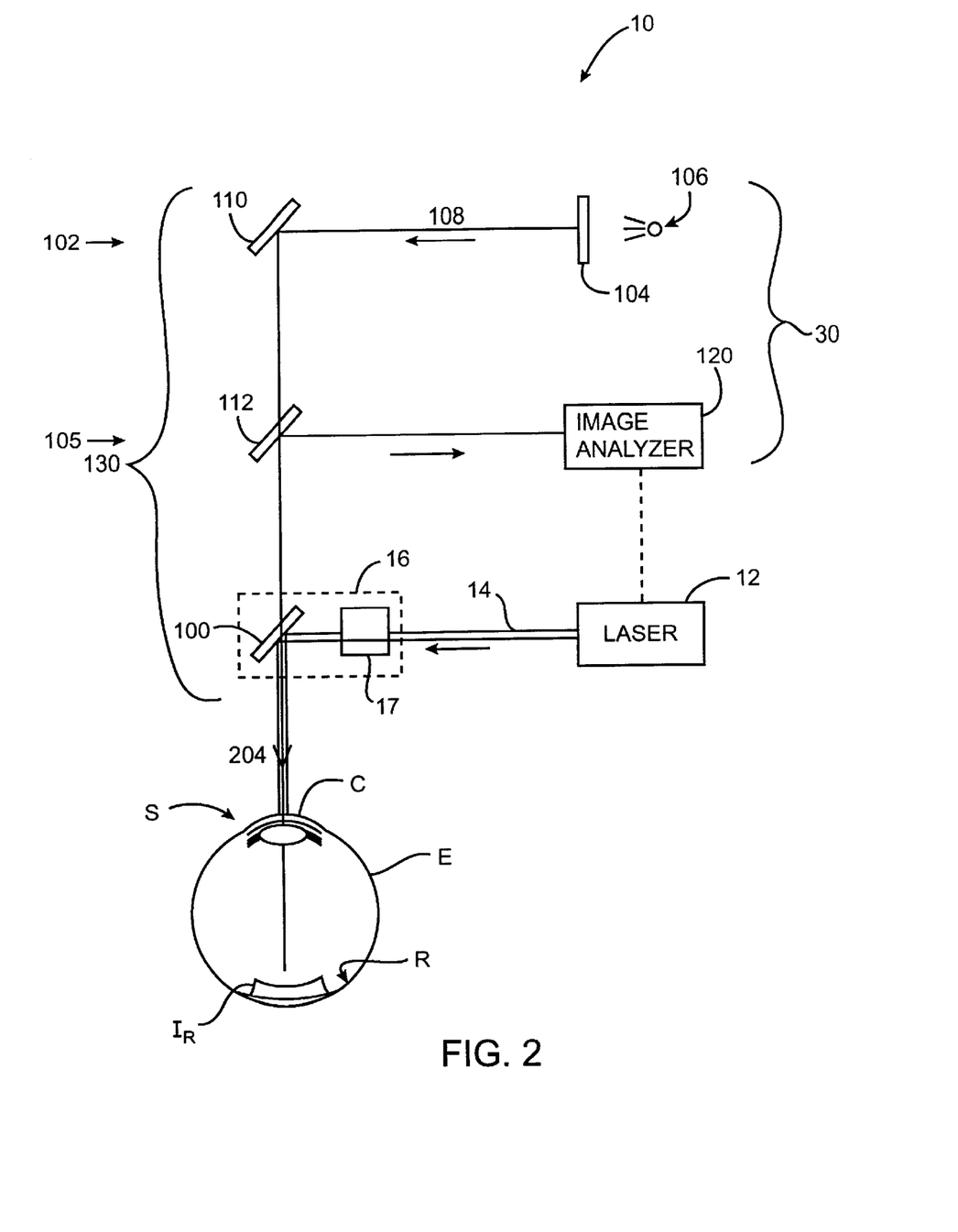
FIG. 2 is a simplified schematic of the laser eye surgery system of the present invention.

Referring now to FIG. 2, a simplified schematic of the laser eye surgery system 10 shows the optical components used in an optical feedback system 30. Laser 12 directs the laser beam 14 at a beam splitter 100 of the laser delivery optical system 16, often via ablation patterning means 17. As described above, ablation patterning means 17 may include scanning mechanisms (such as offset lenses, mirrors, prisms, or the like), variable profiling mechanisms (such as variable diameter iris diaphragms, variable width slits, zoom lens systems, selectable masks, or the like) and/or energy tailoring mechanisms (such as ablatable masks or gels, diffractive optics, or the like). Beam splitter 100 redirects beam 14 and its pattern of ablation energy towards the eye E to reshape cornea C. This resculpting of cornea C will often be performed after removing or displacing an epithelial layer of the cornea and/or a flap including epithelial tissue, Bowman's Membrane, and stromal tissue (as is well described in the patent literature), or may possibly be focussed through the epithelial layer and Bowman's Membrane with an intrastromal system. To provide feedback regarding the effects of the laser ablation procedure on the eye, system 10 generally includes projection optics 102 and imaging optics 105 arranged to project onto and image from a surface of a retina R of eye E. As seen in FIG. 2, at least some of the optical components of projection system 102, imaging system 105, and laser delivery system 106 may be used by more than one of the systems.

In addition to cornea C, eye E includes a number of other components which will affect the eye's overall optical performance, including the lens, iris, anterior and posterior chambers, etc. These and the other optical components of the eye, including cornea C, are generally referred to herein as the ocular optical system S. To provide feedback on the actual results of the resculpting of cornea C, and advantageously, on the changes in optical properties of the overall ocular optical system S, optical feedback system 30 both projects and images an image $I_R$ on retina R of eye E.

Figure 3A:
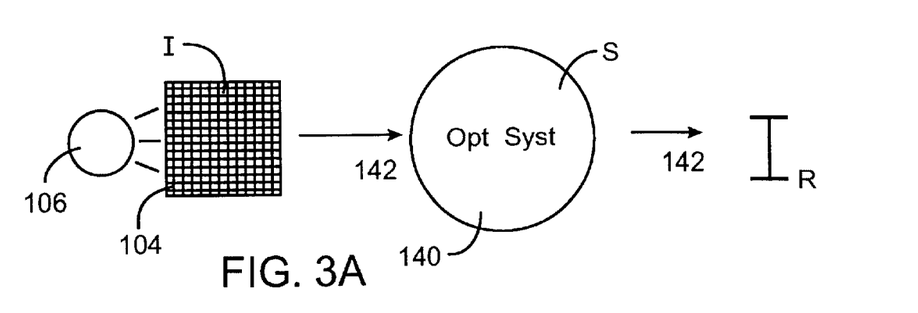
FIGS. 3A and 3B are functional block diagrams schematically showing systems and methods for measuring quality of a corneal by projecting and imaging an image through the corneal optical system.

As can be understood with reference to FIGS. 2 and 3A, a target object 104 (which defines a reference image I) is used to project image I on the retina of the eye E to form retinal image $I_R$. The object 104 may be self-illuminating or have an energy source 106 such as a light emitting diode, a laser diode, or a light bulb to direct light rays 108 carrying the reference image I from object 104 towards the eye E. A beam splitter 110 may be used to direct the energy rays towards the eye E. The reference image $I_R$ may also be projected using energy outside of the visible spectrum, such as (but not limited to) infrared energy.

The imaging quality of retinal image $I_R$ will vary with the quality of the total optical system through which the projected reference image I travels, including the optical elements of the image projection system 102 and the ocular imaging system S of eye E. As can be understood with reference to FIGS. 4–5C, the object 104 may assume a variety of configurations such as reflective or transparent planar bodies, the object often defining a reference image as a grid, a set of sinusoidal wave gratings, an array of contrast bars of varying size, a Siemen's star, or the like.

Figure 3B:
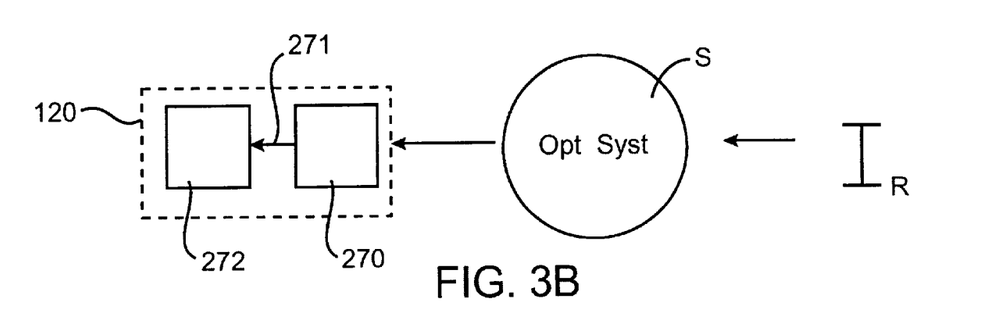
Figure 5A:
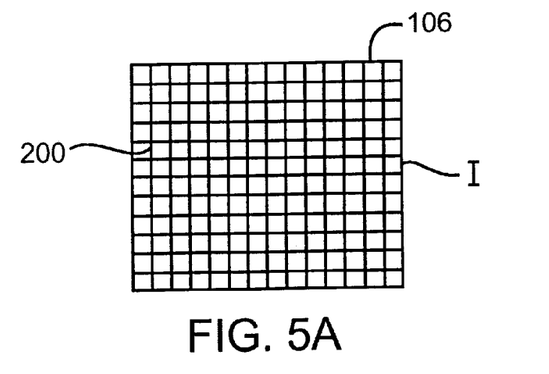
FIGS. 5A–C illustrate alternative reference images and/or evaluation images formed by projecting a reference image onto a retina through the optical system of the eye and by imaging the projected image from the retina through the ocular system.
Figure 5B:
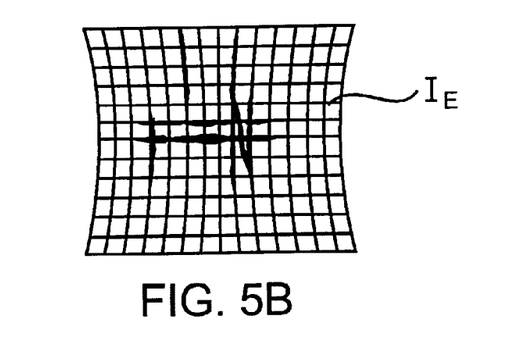

As can be understood with reference to FIGS. 2 and 3B, the retinal image $I_R$ projected in the interior of the eye E is imaged by a retinal image analyzer 120 (optionally via another beam splitter 112) to define an analysis image $I_E$ (see FIG. 5B). Based on the evaluation image $I_E$ imaged from the retina, the image analyzer 120 can be used to determine the current status of the ocular systems.

Image analyzer 120 will often comprise an image capture device 270 such as a charge-couple device (CCD), which converts the evaluation image into digital image signals 271 so that the image information can be analyzed by an image processor 272. Image Processor 272 will typically comprise hardware, software, and/or firmware arranged to calculate an optical characteristic of the evaluation image $I_E$ in response to image signals 271. Image Processor 272 will often determine optical quality, optionally by measuring the smallest features or spatial frequencies which are accurately reproduced in the evaluation image $I_E$. More complex analysis may also be provided. The image processor 272 may be described as being an optical transfer function calculation device, a modulation transfer function calculation device, or the like, depending on which quality measurement is used within the system.

Advantageously, the image analyzer 120 can provide real time and/or intermittent information about a vision correction procedure before, during, and/or after the laser surgery procedure, as the projection optics 102 and imaging optics 105 do not interfere with the operation and/or alignment of the laser 12. Optionally, feedback during a resculpting may be provided while ablation is taking place and/or between pulses or partial treatments (to improve signal-to-noise performance) as object 104 and feedback assembly 120 are both upstream of the beam splitter 100 within the optical train 130. Preferably, the beam splitter 100 is an ultraviolet beam splitter which does not interfere with visible light rays and/or infrared energy coming from object 104.

Although the retinal image analyzer 120 may operate on a variety of different principles, a preferred embodiment of the analyzer 120 uses an optical transfer function (OTF) to determine a quality of the imaging provided by the corneal optical system S. The optical transfer function is a general measure of how well an optical system can transmit or transfer an image.

In general terms, the light or energy from an object 104 passing through an optical system 140 as indicated by arrows 142 will be produce an image of the object. In a perfect optical system, an image of object 104 would be perfectly recreated after passing through the optical system 140. In real systems, however, aberrations in any of the components of optical system 140 cause distortion and diffraction that create a less than perfect image transfer. Analysis of the image ($I_R$ in our example) that is actually created by the optical system allows the quality of the optical system to be accurately measured. More specifically, by analyzing the retinal image $I_R$, and particularly by comparing the retinal image $I_R$ to the reference image I, an optical transfer function of optical system 140 can be determined. As the optical properties of the optical train 130 of system 10 can be readily determined, this allows the optical quality of the ocular optical system to be calculated. While the optical transfer function is a particularly advantageous measurement of optical imaging quality, it should be understood that a wide variety of known alternative optical quality measurements might be calculated.

Optical feedback system 30 will typically not derive the optical transfer function (or any other alternative measurement of imaging quality) directly from the retinal image $I_R$, but will instead measure the imaging quality of the ocular optical system by imaging the retinal image $I_R$ from the retina onto the image capture device 270, so that the image again passes through the ocular optics. Thus, the final evaluation image $I_E$ will be defined by a reference image I which has passed twice through cornea C and the other components of the ocular optical system.

Theoretically, the optical transfer function may be defined by:

$$OTF = MTF \cdot PTF$$

Figure 4:
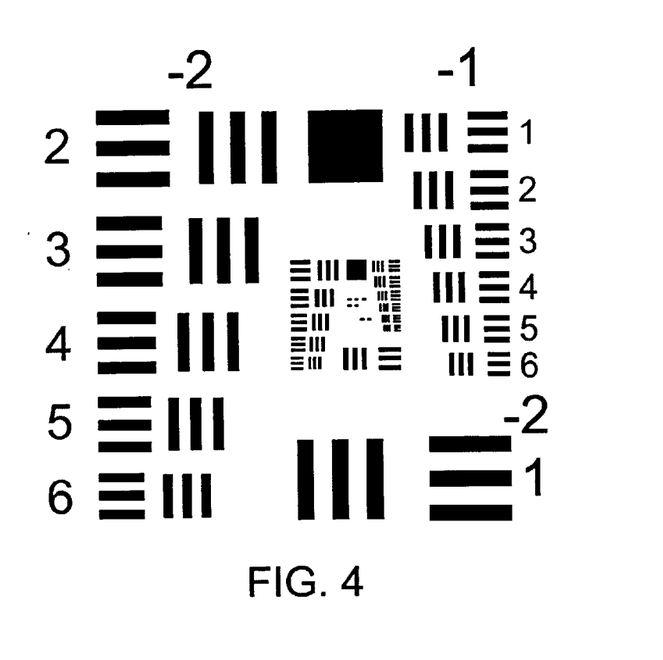
FIG. 4 shows a reference image for use in the present invention.
Figure 5C:
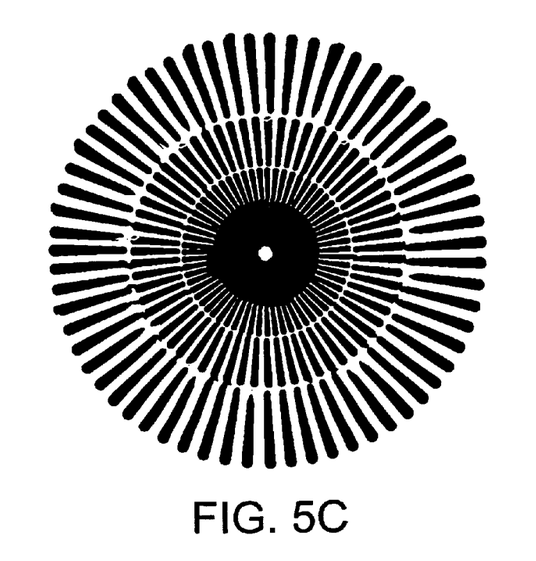

In other words, the optical transfer function is the product of a modulation transfer function (MTF) and a phase transfer function (PTF). The modulation transfer function describes the way that the optical system 140 transfers contrast or modulation from object 104 to image I, as a function of spatial frequency. It relates to amplitude and intensity. The modulation transfer function is defined as:

$$MTF = \frac{I_{max} - I_{min}}{I_{max} + I_{min}}$$

where $I_{max}$ and $I_{min}$ are respectively, the maximum and minimum values of brightness in the object or illumination in the image. The object 104 typically defines an image I as a pattern of lines with spatial separations or frequencies which vary according to a known pattern. A variety of these patterns are shown in FIGS. 4, 5A, and 5C. Typically, square wave gratings are used since they are easier to make, although their use often involves more data processing to extract the sinusoidal components used in MTF. Optionally, the modulation transfer function alone may be used as a measurement of imaging quality.

In a perfect optical system, the modulation transfer function approaches one. The modulation transfer function, also known as the sine wave response and contrast transfer function, measures the ability of an optical system to reproduce or transfer various levels of detail from the object to the image, as shown by the degree of contrast (modulation) in the image. As one might expect, the finer the detail, the higher the contrast required to resolve it.

The second component of the optical transfer function is the phase transfer function (PTF). It relates to image distortion or phase, and may optionally be disregarded when calculating the optical quality of the optical system. If used, the phase transfer function may be defined as follows:

$$PTF = e^{i(\delta' - \delta)},$$

with $\delta$ and $\delta'$ being the phase of the reference image and evaluation image, respectively.

Advantageously, the optical transfer function and/or modulation transfer function of an optical system can directly be determined by imaging gratings through the optical system. The contrasts in the object or reference image I and the evaluation image $I_E$ are measured, and their ratio can define the modulation transfer function for the spatial frequency of the grating. Similarly, imaging quality may be measured by determining the resolution power of the optical system, such as by measuring the smallest detail that can be detected or discriminated in an image. This is typically done by imaging a resolving power chart or image, such as the bar target resolution chart shown in FIG. 4, the Siemen's Star shown in FIG. 5C, or the like. Such measurements may optionally account for the effects of chromatic aberration, off-axis distance, orientation of the reference image, and the like.

Still further optical imaging quality measurement calculation methods might be used, such as determining the contrast threshold function, and the like. These and other standard optical imaging quality measurements are known and are described, for example, by George Smith et al. in "*The Eye and Visual Optical Instruments,*" Cambridge University Press (1997) pp. 662–691, by F. W. Campbell et al. in "*Optical Quality of the Human Eye,* " *J. Physiol.*, 186 (October 1966), pp. 558–578; "*Photonics Dictionary,*" pp. D-22, 92, 102, and 123 (1997); and by William D. Stanley et al. in "*Digital Signal Processing,*" 2d Ed., (1984) pp.120–124; the full disclosures of which are incorporated herein by reference.

Referring now to FIGS. 2, 5A, and 5B, the object 104 illuminated by light source 106 is shown to have a square grading pattern 200. Energy rays from the object 104 pass through various optics 130 in the laser system and head towards the eye E as indicated by arrows 204. The retinal image $I_R$ created on the retina of the eye E is reflected by the beam splitter 112 towards the imaging analyzer 120. As the optical system of the eye is not a perfect optical system, transmitting the image through ocular optical system S will not exactly reproduce the reference, but will instead result in some loss of resolution and some distortion of the image. Hence, the imaged evaluation image $I_E$ shows some loss in contrast where there is some blurring of the adjacent elements. Such changes should be indicated by the value of the optical transfer function, modulation transfer function, or the like. The reduction in contrast and change in phase measured by the optical transfer function indicates that the optical system contains aberrations and other defects, which might, for example, be indicated by an OTF value of significantly less than 1.0.

The schematic evaluation image $I_E$ of FIG. 5B also exhibits distortion of the square grading pattern, where the originally square grading pattern 200 now has an hour-glass shape. The optical transfer function can take this change into account as it measures the quality of the optical system 140. Additionally, by analyzing the evaluation image and comparing the evaluation image with the original reference image, the optical errors of the optical system 140 (and hence the ocular optics S) can be derived.

Using standard post image processing techniques such as fast fourier transforms, filtering techniques, and known optical transform image modulation techniques originally developed for detecting, measuring, and compensating for atmospheric pollution, image processor 272 may optionally comprise a computer image restoration and analysis processor which calculates the spherical, cylindrical, and/or other distortion of the ocular optical system. Suitable algorithms for use in such a processor are now used to correct for atmospheric distortion of land-based telescopes viewing distant stars or planets. By comparing the evaluation image $I_E$ to the reference image I, these computational tools could be used to calculate the optical errors of the ocular optical system. Once again, such a system should account for both the first pass of the reference image through the ocular system en route to the retina, and for the second pass-through the cornea, lens, and other ocular components of the eye en route to the CCD. Calculation of a resculpting of the cornea to compensate for the measured aberration would then be relatively straightforward, optionally providing feedback to the laser treatments system resulting in a revised ablation pattern. Software packages for such post image processing techniques are commercially available, such as the Interactive Data Language™ software from Research Systems Inc. of Boulder, Colo.

Figure 6A:
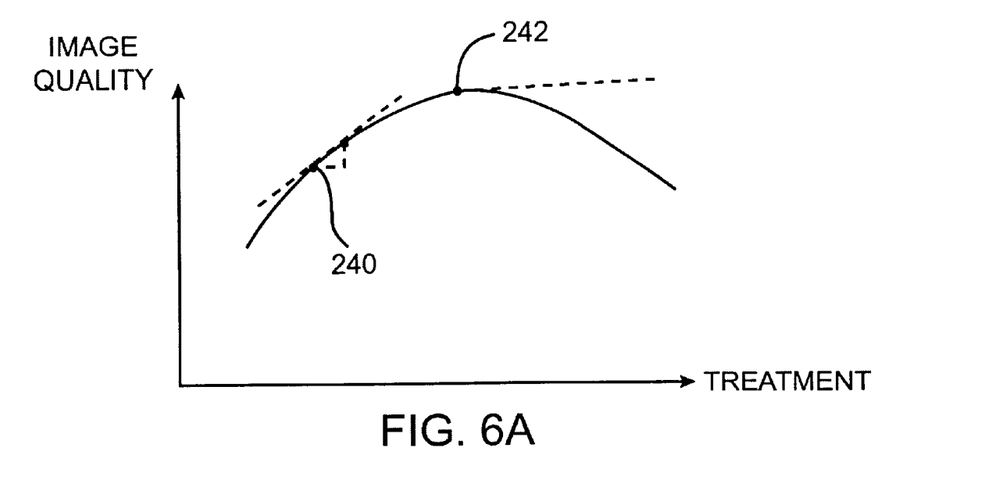
FIGS. 6A and 6B schematically illustrate how monitoring of the image quality and/or the rate of change of the image quality can provide feedback during treatment of and eye using the system of FIG. 1.
Figure 6B:
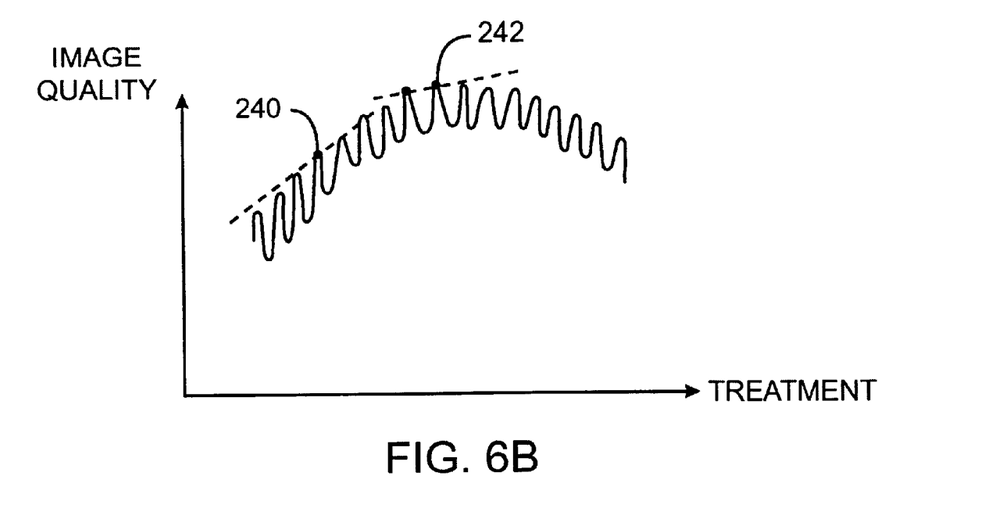

A simpler feedback control system may track the progress of optical quality of the ocular optical system during a predetermined ablation pattern, as can be understood with reference to FIGS. 6A and 6B. By charting the optical transfer function or other image quality measurement relative to a treatment time, treatment energy, number of partial treatment scans, or the like, the graph can be used to show when the optical system has reached its maximum level of improvement.

As seen in FIG. 6A, calculating a slope or rate of change of the image quality allows the operator and/or system to proceed when the treatment continues to improve vision at a significant rate 240, and to halt treatment when the rate of improvement of the imaging quality is at or near zero, ideally below some predetermined rate 242. Monitoring of the rate of change of the imaging quality allows the system to rely on any arbitrary image quality measurement scale, and also simplifies compensation for the two-pass transmission through the ocular optics, as a significant rate of change in the ocular optics will correlate with a significant rate of overall image quality change of the evaluation image. Similarly, when the rate of change of the image quality of the evaluation image is at or near zero, this indicates that the ocular optics are no longer significantly improving with continued treatment, and treatment can be halted before any deterioration of visual acuity from overtreatment.

Figure 7:
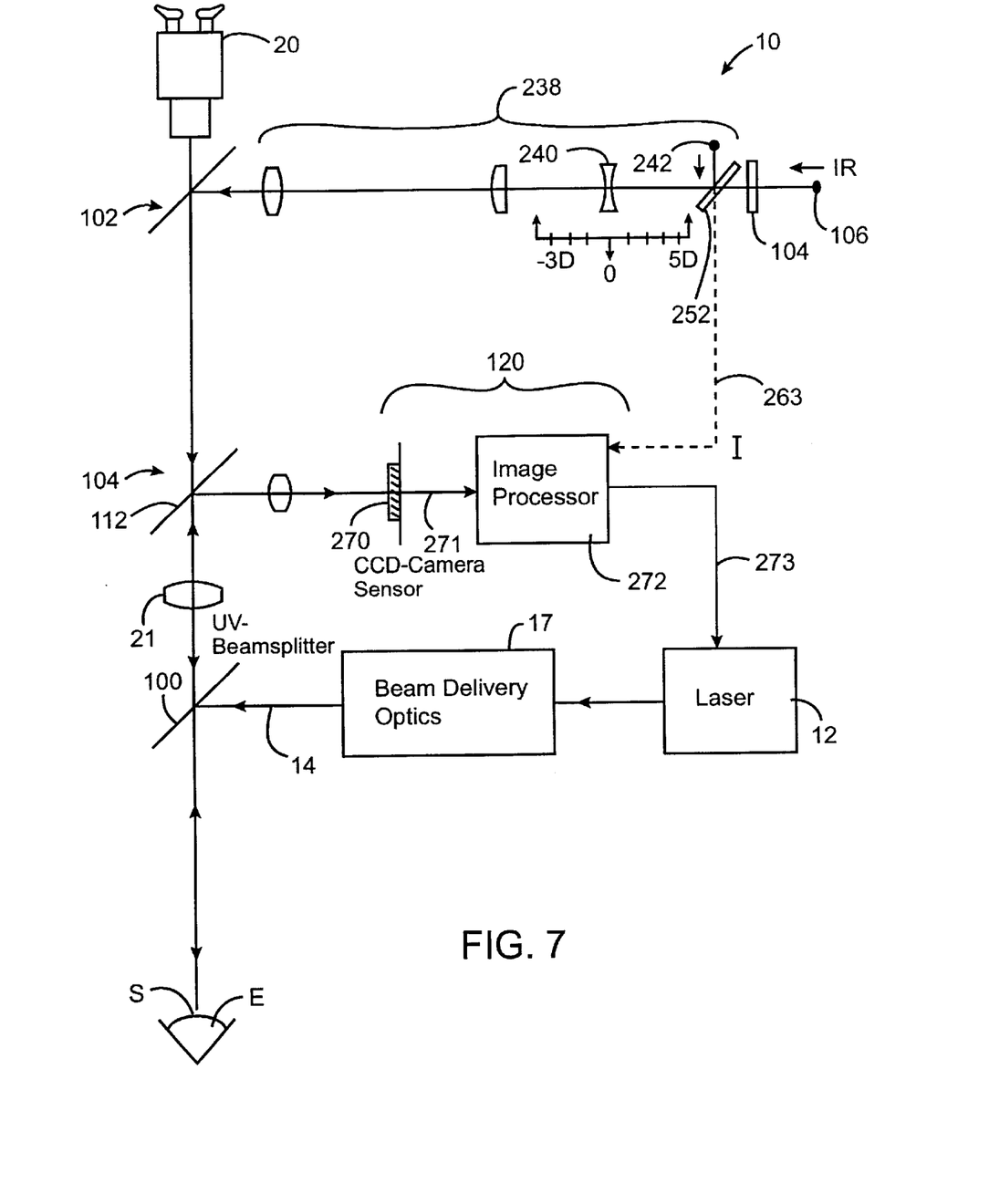
FIG. 7 shows a more detailed schematic of an exemplary embodiment of the present invention.

The rate-based feedback technique of FIG. 6A may be easily incorporated into known laser eye surgery systems. Referring now to FIGS. 1 and 7, some or all of the optical components of microscope 20 (such as an objective 21) may be used to image the retina of eye E (and the projected retinal image $I_R$ from projection optics 102), often by providing sufficient travel of the microscope body, alternative microscope ocular lenses to increase the microscope working distance, and the like. In some embodiments, the image analyzer may simply be mounted on a camera pad of the microscope generally provided for an assistant display system.

In general, the retinal image feedback assembly can use a charge-coupled device (CCD) image capture device 270 to detect the retinal image from the interior of the eye E, the CCD ideally having a high resolution CCD camera such as those commercially available from the Eastman Kodak Company under the model name Megaplus™. The exemplary CCD will have a resolution of about 6 million pixels or more.

Data from image capture device 270 will be transmitted to and processed by an image processor 272, with the image processor optionally being incorporated into processor 22 which controls the delivery of the ablative laser energy pattern to the eye (see FIG. 1). Alternatively, the image processor may comprise a dedicated processor board, or a wide variety of distributed data processing techniques may be employed. In some embodiments, the system operator may evaluate the image manually by viewing the image through microscope 20, halting the procedure by actuating a food pedal, a touch screen, a mouse, a voice input device, or any other input device. Regardless, the evaluation image from the imaging optics 104 will be used to determine a quality of the imaging system, such as by determining the smallest discrete spatial frequency of the parallel bar reference image of FIG. 4 which remains distinct in the evaluation image, or by any other known image quality calculation technique. Such evaluations often make use of the information regarding the reference image, optionally comparing the evaluation image $I_E$ with the reference image to calculate quality, as schematically illustrated by path 263.

As imaging quality can be measured repeatedly during or between treatments without excessive delay of the treatment process, the change in the measured imaging quality with a desired unit of treatment may be calculated as shown in FIGS. 6A and 6B. When the improvement in imaging produced from a unit of treatment is less than a nominal value, a feedback signal may be sent via a feedback path 273 to laser 12, laser delivery optics 16, and/or laser controller 22 to terminate the ablation. As can be understood with reference to FIG. 6B, selection of the proper measurement sampling time may help to compensate for transient changes in imaging quality during, for example, incomplete or uneven scans of the laser during a series of partial treatments. Regardless, by measuring the rate of change of the actual imaging quality of the ocular imaging system, the operator can proceed to and stop at the maximum optical imaging quality, thereby reducing the likelihood of follow-up or touch-up treatments.

Figure 8:
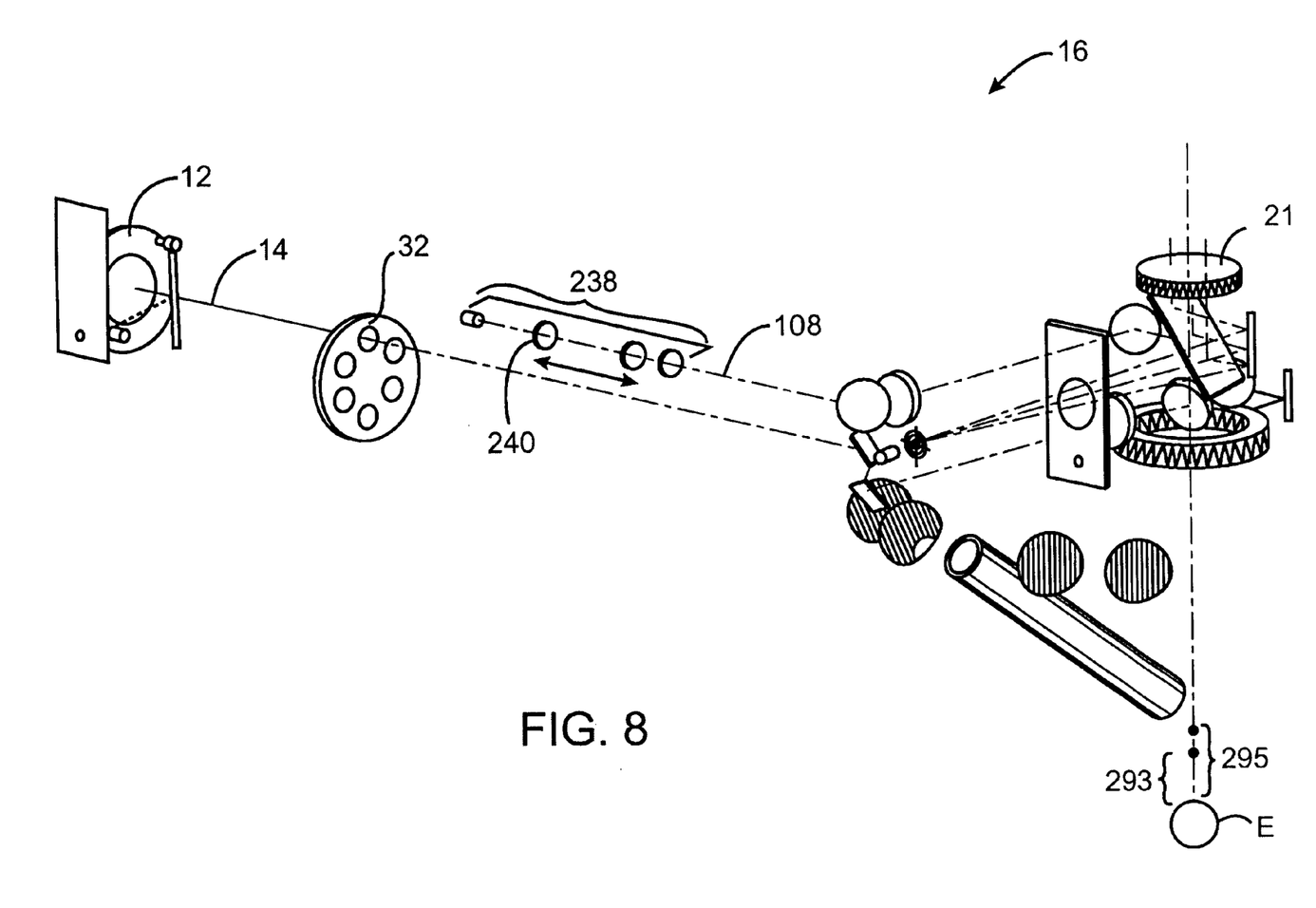
FIG. 8 illustrates an optical feedback system according to the principles of the present invention, in which the projection system makes use of components which are also used to provide a variable fixation target for viewing by the patient to help maintain alignment between the eye and the treatment system.

Still further components of optical feedback system 30 may be incorporated into existing systems of known laser eye surgery devices. For example, as illustrated in FIGS. 7 and 8, and as more fully described in commonly assigned, copending U.S. patent application Ser. No. 09/105,690 (filed on Jun. 26, 1998, the full disclosure of which is incorporated herein by reference), it is generally beneficial to provide a viewing target system 238 for the patient to view during a laser treatment so as maintain alignment between eye E and the treatment axis of the laser delivery system. As the optical characteristics of the eye will change during the procedure, target system 238 can include one or more moveable lens 240 to compensate for a refractive error of the eye so that a fixation target 242 appears in focus to the patient. At least some of the components of target system 238 may be used to project the reference image onto the retina as a projection system 102. As the position of the movable lens 240 to properly compensate for known refractive errors can be determined, by moving the lens to the position providing the best retinal image quality, the refractive error of the eye may be accurately measured.

FIG. 7 shows an exemplary active patient fixation optical system which allows the patient to maintain a steady eye position during the surgical procedure. The patient fixation optical system uses a light emitting diode (LED) as a target 242 for a patient to watch. By coordinated movement of movable lens 240, the active fixation system maintains the LED in focus to the patient even though the optical characteristics of the eye is changing during the surgery procedure. By maintaining the LED in focus, the patient can more vigilantly maintain their focus on the LED and thus reduce random eye movement. The active patient fixation optical system 238 uses a beam splitter 252 to project the LED in front of the object 104. In the situation where the fixation optical system 238 is in use, it will be desirable to illuminate the target 104 with infrared energy from the source 106. In this manner the patient will only see the LED and not be confused by visible light from the light source or object 104. In some embodiments, a single light source and/or image may be used for both fixation and reference image projection.

As the laser selectively removes portions of the cornea, aberrations may be temporarily ablated on the eye. To decrease any deleterious effects of the aberrations on the patient's vision (which might temporarily limit the patient's ability to focus on the visual fixation target, and possibly inflicting correctable damage to the eye sight if the ablation process has to be permanently terminated before completion), a refractive treatment may be broken into a series of treatments which incrementally improve a refractive defect of the eye. Even where these sub-treatments are performed immediately following one another, this method of breaking the treatment into a series of smaller corrections will minimize aberrations created during the ablation process. This aspect of the present invention is schematically illustrated in FIG. 9 with 290a, 290b, and 290c representing incremental changes in the shape of the cornea.

Figure 9:
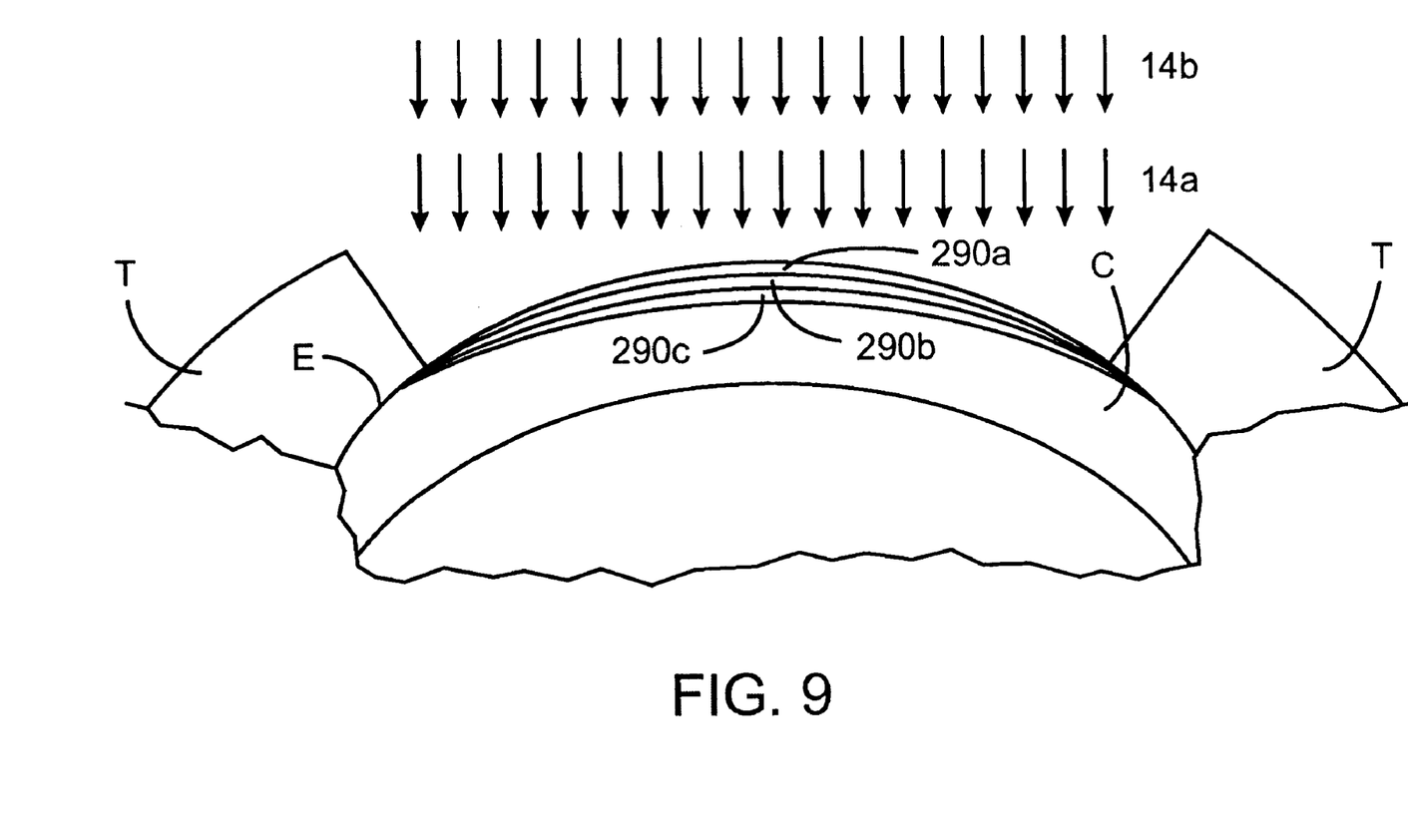
FIG. 9 schematically illustrates incremental removal of corneal tissue according to the principles of the present invention.

As seen in FIG. 9, the epithelium T will generally be displaced to reach the cornea. The epithelium may be removed by manual scraping or abrasion, or the cornea may simply be incised to define a flap, with the flap being folded out of the way during ablation of the underlying stroma.

The exposed stromal surface will not provide an ideal optical surface, so that the overall imaging quality of the ocular optics may not be close to ideal during resculpting. Nonetheless, while the removed or displaced epithelium or flap will degrade optical quality, it may not significantly alter the resculpting to maximize quality and/or the rate of change of quality during a procedure, so that the amount of treatment to achieve the maximum optical performance without the epithelium or flap in the corneal optical system may not be significantly different than the amount of treatment desired to achieve the maximum healed optical performance. Even if the optical error of the optical system without the epithelium differs significantly than the healed optical error, the system of the present invention may be used to measure an actual total change in the optical characteristics of the eye, for example, by repeatedly refocusing the retinal image with movable lens 240, and by measuring the total movement of the movable lens throughout a procedure. The procedure might be terminated when the lens movement showed that a desired amount of resculpting had been achieved.

As schematically illustrated in FIG. 9 patient with a spherical refractive error of minus ten (−10) diopters can be corrected with a series of two diopter corrective treatments. The imaging system will initially project a target to the separation distance corresponding to the −10.0 D position, that is, for myopia, at a separation distance 293 of 0.1 meters in front of the patient. A first series of laser pulses 14*a* selectively removes a first portion 290*a* of stroma S, thereby effecting a two diopter correction of the patient's myopia. At this point, the target can projected to a different separation distance 295 appropriate to −8.0 D of myopia, which would be 0.125 meters in front of the plane of the patient's eye.

Referring now to FIGS. 7, 8 and 9, the target separation between Eye E and the evaluation image $I_E$ and/or fixation target image will generally be varied by moving lens 240. Optionally, a position of lens 240 may be controlled and/or sensed by image analyzer 120. In some embodiments, the system operator may manually move the lens to focus the evaluation image $I_E$ while viewing the evaluation image via microscope 20.

An optical characteristic of ocular optics S will generally be determined after at least partial treatment of eye E, optionally in response to the focused evaluation image. The optical characteristic will often comprise imaging quality, which may be measured by an image analyzer 120, or simply by the system operator evaluating the smallest spatial frequency, which can be distinguished via microscope 20. More detailed optical characteristics of the ocular system may also be determined, as described above. In some embodiments, optical quality measurements might be taken with the projection system 102 fixed at a separation distance appropriate for fully corrected vision. Feedback signals will often be transmitted along feedback path 273 in response to the measured quality or other optical characteristic.

In our exemplary −10.0 D treatment procedure, the optical characteristic should indicate improvement in the spherical error after the first partial corrective treatment, so laser system 10 will proceed with an additional series of pattern of laser pulses 14*b* to further reduce myopia. Additional measurements of the optical characteristic of ocular optics S may again be made after this partial treatment. If the treatment continues to benefit optical quality as planned, further partial treatments may proceed, the partial treatments optionally being interspersed with optical quality measurements. Smaller treatment increments (for example, 1.0 D or less) may be imposed when resculpting approaches completion. When optical quality no longer improves with treatment, that is, when the rate of change of optical quality is at or near 0.0, treatment will halt in response to feedback signals 273. Optionally, the partial treatments might also be modified in response to the feedback signals, for example, increasing the depth of ablation if the measured optical characteristic indicate an intended 2.0 D partial treatment actually results in only a 1.7 D change in the ocular optical system.

As the laser ablates the cornea and alters the refractive configuration of the eye, the adjustable optical train varies the separation distance under the dynamic control of the computer so that the image of the target, as viewed by the patient, remains substantially in focus. The laser resculpting process will typically take between about 10.0 secs. and 3.0 mins. to complete, and the delivery optics of the laser surgery system will also often be computer controlled. Adjustment of the adjustable optical train may be based on real time topographical measurements of the cornea during the photoablation process. Alternatively, the adjustable optical train will be varied by the computer per calculated intermediate configurations of the eye during resculpting.

While the exemplary embodiment has been described in some detail, by way of example and for clarity of understanding, a variety of modifications, changes, and adaptations will be obvious to those of skill in the art. For example, the system may also use multiple images, colors, or patterns in the feedback system. Movable and/or selectable lens elements may be included in the projection system to compensate for and measure cylindrical (as well as spherical) errors and changes in the eye. Hence, the scope of the present invention is limited solely by the appended claims.

What is claimed is:

1. An eye treatment system for performing vision correction on an eye, the eye having a retina and ocular optics including a cornea, the system comprising:

projection optics which project a reference image through the ocular optics and onto the retina when the eye is positioned for treatment;

imaging optics which acquire an evaluation image from the retina through the ocular optics, the evaluation image defined by the reference image as projected through the ocular optics and as imaged through the ocular optics; and an energy transmitting element positioned relative to the imaging optics to transmit treatment energy toward the cornea for altering the ocular optics of the positioned eye.

2. The eye treatment system of claim 1, wherein at least a portion of the projection optics or at least a portion of the imaging optics are coaxially aligned with the treatment energy.

3. The eye treatment system of claim 2, wherein the energy transmitting element comprises a laser and the energy comprises a corneal ablation laser beam having a beam path, and further comprising a first beam splitter separating an imaging path of the imaging optics from the beam path.

4. The eye treatment system of claim 3, further comprising a second beam splitter separating the imaging path from a projection path of the projection optics, at least a portion of the projection optics and at least a portion of the imaging optics being coaxially aligned with the beam path of the laser beam.

5. The eye treatment system of claim 4, wherein the first beam splitter is disposed between the eye and the second beam splitter.

6. The eye treatment system of claim 1, wherein the imaging optics comprise at least some of the optical components of a microscope.

7. The eye treatment system of claim 6, wherein the microscope can acquire an image of the cornea for optically directing a corneal resculpting procedure.

8. The eye treatment system of claim 6, wherein the reference image is adapted to indicate a quality of the corneal optics, and further comprising an input coupled to the energy transmitting element for terminating the treatment energy at a predetermined rate of change of the imaging quality.

9. The eye treatment system of claim 6, wherein the imaging optics further comprise an imaging beamsplitter separating a microscope optical path from the imaging path.

10. The eye treatment system of claim 1, further comprising an image capture device optically coupled to the imaging optics and generating analysis image signals in response to the evaluation image, and an image analyzer coupled to the image capture device, the image analyzer determining an imaging quality of the ocular optics in response to the analysis image signals.

11. The eye treatment system of claim 10, wherein the image analyzer is coupled to the energy transmitting element to define a corneal treatment feedback path, the energy transmitting element altering the treatment energy in response to feedback signals from the feedback path.

12. The eye treatment system of claim 10, further comprising a reference object defining the reference image, wherein the image analyzer compares an image of the reference object with the evaluation image to determine the imaging quality.

13. The eye treatment system of claim 10, wherein the analyzer further determines a rate of change of the imaging quality.

14. The eye treatment system of claim 13, wherein the rate of change of the imaging quality indicates a slope of the quality of the image relative to a unit of the treatment directed to the cornea.

15. The eye treatment system of claim 13, further comprising an input coupled to the energy transmitting element for terminating the treatment energy at a predetermined rate of change of the imaging quality.

16. The eye treatment system of claim 10, wherein the analyzer is adapted to calculate the imaging quality using a modulation transfer function.

17. The eye treatment system of claim 1, wherein said projection optics create an infrared image on the retina of the eye.

18. The eye treatment system of claim 1, wherein said energy transmitting element comprises a laser producing an energy beam in the ultraviolet spectrum.

19. The eye treatment system of claim 1, wherein said energy transmitting element comprises an excimer laser.

20. The eye surgery system of claim 1, wherein said energy transmitting element comprises a solid state laser.

21. The eye surgery system of claim 1, wherein the image capture device comprises a high resolution CCD.

22. The eye surgery system of claim 1, wherein the projection optics include at least one movable element to adjust an imaging distance between the eye treatment system and the projected reference.

23. The eye surgery system of claim 22, further comprising a patient fixation target system including at least a portion of the projecting optics, the target system capable of directing a fixation target toward the eye for viewing by the eye so as to help maintain axial alignment between the eye and the treatment energy.

24. An eye treatment system for performing vision correction on an eye having a retina disposed behind ocular optics, the ocular optics including a cornea, the system comprising:

projection optics which project a reference image through the ocular optics and onto the retina;

imaging optics which acquire an evaluation image from the retina through the ocular optics, the imaging optics defining an path;

an image capture device optically coupled to the imaging optics and generating analysis image signals in response to the evaluation image;

an image analyze coupled to the image capture device, the image analyzer determining an imaging quality of the ocular optics in response to the analysis image signals; and a corneal ablation laser system directing a laser beam toward the cornea for altering the ocular optics, at least a portion of the laser beam being substantially coaxially aligned along at least a portion of the imaging path, the laser system coupled to the image analyzer along a corneal treatment feedback path, the laser system altering the laser beam in response to feedback signals from the feedback path.

25. An eye treatment system for performing vision correction on an eye, the eye having a retina and ocular optics including a cornea, the system comprising:

projection optics which project a reference image through the ocular optics and onto the retina when the eye is positioned for treatment, wherein the reference image is adapted to indicate a quality of the corneal optics;

imaging optics which acquire an evaluation image from the retina through the ocular optics, the evaluation image defined by the reference image as projected through the ocular optics and as imaged through the ocular optics, wherein the imaging optics comprise at least some of the optical components of a microscope;

an energy transmitting element positioned relative to the imaging optics to transmit treatment energy toward the cornea for altering the ocular optics of the positioned eye; and an input coupled to the energy transmitting element for terminating the treatment energy at a predetermined rate of change of the imaging quality.

* * * * *